US012692979B2

(12) United States Patent
Kakosimos et al.

(10) Patent No.: US 12,692,979 B2
(45) Date of Patent: Jul. 28, 2026

(54) METHOD OF DETECTING LUBRICANT DEGRADATION IN AN ELECTRICAL MACHINE

(71) Applicant: ABB Schweiz AG, Baden (CH)

(72) Inventors: Panagiotis Kakosimos, Västerås (SE); Olli Alkkiomäki, Helsinki (FI); Teija Aaltonen, Helsinki (FI)

(73) Assignee: ABB SCHWEIZ AG, Baden (CH)

( * ) Notice: Subject to any disclaimer, the term of this patent is extended or adjusted under 35 U.S.C. 154(b) by 444 days.

(21) Appl. No.: 18/257,634

(22) PCT Filed: Dec. 22, 2020

(86) PCT No.: PCT/EP2020/087659
§ 371 (c)(1),
(2) Date: Jun. 15, 2023

(87) PCT Pub. No.: WO2022/135699
PCT Pub. Date: Jun. 30, 2022

(65) Prior Publication Data
US 2024/0044449 A1      Feb. 8, 2024

(51) Int. Cl.
*F16N 29/00*          (2006.01)
*G01N 33/28*          (2006.01)
(52) U.S. Cl.
CPC ......... *F16N 29/00* (2013.01); *G01N 33/2888* (2013.01); *F16N 2210/14* (2013.01); *F16N 2210/18* (2013.01); *F16N 2250/08* (2013.01)
(58) Field of Classification Search
CPC .... G01N 33/2888; G01M 13/04; F16N 29/00; F16N 2210/14; F16N 2250/08; F16N 2210/18
See application file for complete search history.

(56) References Cited

U.S. PATENT DOCUMENTS

| | | | | |
|---|---|---|---|---|
| 9,109,748 B2 * | 8/2015 | Lakomiak | .............. | G01H 1/003 |
| 10,203,242 B2 * | 2/2019 | Hedin | .................. | G05B 23/024 |

(Continued)

FOREIGN PATENT DOCUMENTS

| | | |
|---|---|---|
| CN | 102301149 A | 12/2011 |
| CN | 105627074 A | 6/2016 |

(Continued)

OTHER PUBLICATIONS

International Search Report and Written Opinion of the International Searching Authority; Application No. PCT/EP2020/087659; Completed: Sep. 29, 2021; Mailing Date: Oct. 8, 2021; 14 Pages.

(Continued)

*Primary Examiner* — An H Do
(74) *Attorney, Agent, or Firm* — Greenberg Traurig, LLP

(57) ABSTRACT

A method of detecting degradation of a lubricant in a bearing of an electrical machine, including: a) obtaining a first outer bearing ring temperature, b) changing the speed of the electrical machine, c) obtaining a second outer bearing ring temperature when the speed has changed, d) determining a thermal response value of the outer bearing ring based on the first outer bearing ring temperature and the second outer bearing ring temperature, e) comparing the thermal response value with a reference thermal response value for the same speed change as in step b), and f) in case the thermal response value differs from the reference thermal response value, concluding that the performance of the lubricant has degraded.

19 Claims, 3 Drawing Sheets

(56)     References Cited

U.S. PATENT DOCUMENTS

| | | | |
|---|---|---|---|
| 11,630,028 B2 * | 4/2023 | Saarinen | G01N 33/2858 |
| | | | 73/61.42 |
| 2011/0265569 A1 | 11/2011 | Ganji et al. | |
| 2019/0072457 A1 | 3/2019 | Isobe et al. | |
| 2019/0234463 A1 | 8/2019 | Lugt et al. | |
| 2019/0271584 A1 | 9/2019 | Hedin | |

FOREIGN PATENT DOCUMENTS

| | | |
|---|---|---|
| CN | 106041639 A | 10/2016 |
| CN | 110107591 A | 8/2019 |
| CN | 110307978 A | 10/2019 |
| JP | H06331458 A | 12/1994 |

OTHER PUBLICATIONS

Chinese Office Action; Application No. 2020801079601; Completed: Mar. 5, 2025; Issued: Mar. 6, 2025; 25 Pages.

* cited by examiner

METHOD OF DETECTING LUBRICANT DEGRADATION IN AN ELECTRICAL MACHINE

TECHNICAL FIELD

The present disclosure generally relates to rolling-element bearings used in electrical machines.

BACKGROUND

Mechanical failures are the most common failures that occur in powertrains. Failures are often attributed to mechanical bearings. Bearing failures are often resulting from loss of lubricant, not by bearing fatigue itself. The lack of lubricant leads to premature wear due to excessive heating, further degrading the lubrication, and finally damaging the bearing.

Rolling-element bearings depend on the continuous presence of a very thin film of lubricant between rolling elements and raceways. If a bearing has insufficient lubrication, or the lubricant has lost its lubricating properties, an oil film with sufficient load-carrying capacity cannot be formed. This results in metal-to-metal contact, which leads to adhesive wear, and then to scoring, galling, seizing, and scuffing.

Acoustic emissions and vibration analysis are means that offer high accuracy in detecting a bearing failure. It is however challenging to detect lubricant insufficiency at an early stage. Also, these approaches may require expensive equipment and complicated methods to be in place, whereas their effectiveness strongly relies on the characteristics of the environment and the sensor.

US20190234463 discloses a rolling bearing arrangement, which includes a sensor element for sensing temperature in the space where the rolling elements are located. From the sensed temperature over time and from the speed over time, via a calculated imposed energy on the grease, a remaining period of the grease lifetime is calculated. The imposed energy is calculated from the profiles of the temperature and speed over time, using a model comprising the geometry of the rolling bearing.

The method relies on a complex model for determining the imposed energy using the temperature and speed profile. It would therefore be desirable to find another solution, which allows for detecting the lubricant performance degradation before a failure emerges.

SUMMARY

A general object of the present disclosure is to provide a method that solves or at least mitigates the problems of the prior art.

The present inventors have found that the outer ring temperature exhibits two distinct phases, i.e., before and after a failure occurs. In the first phase, the temperature decreases as the lubricant performance degrades. In the second phase, if the motor is kept in operation under these conditions, the inner and outer raceways, as well as the balls, wear out. As a result, the temperature in the outer ring reaches higher levels. It has thus been found that the absence of or a degraded performance of the lubricant leaves a footprint in the temperatures and allows detecting lubricant issues in an early stage.

The initial decrease in temperature is attributed to the temperature being affected more by the fan speed change of the fan of the electrical machine than by the heat transferred from the rolling elements of the bearing.

There is hence according to a first aspect of the present disclosure provided a method of detecting degradation of a lubricant in a bearing of an electrical machine, comprising: a) obtaining a first outer bearing ring temperature, b) changing the speed of the electrical machine, c) obtaining a second outer bearing ring temperature when the speed has changed, d) determining a thermal response value of the outer bearing ring based on the first outer bearing ring temperature and the second outer bearing ring temperature, e) comparing the thermal response value with a reference thermal response value for the same speed change as in step b), and f) in case the thermal response value differs from the reference thermal response value, concluding that the performance of the lubricant has degraded.

By changing the speed of the electrical machine, temperature variations in the outer bearing ring can be detected. The inventors have also found that the absolute temperature after a speed change cannot be trusted, because there may be other reasons that play a role in the change of the temperature, such as the operation of the electrical machine fan, ambient temperature changes, internal motor faults, operating conditions, etc. An intentional speed change also leaves the current essentially constant. Lubricant degradation can thereby be isolated by the analysis of the thermal response value.

The decrease in second outer bearing ring temperature may be in terms of a lower temperature than the first outer bearing ring temperature, or lower than a reference second outer bearing ring temperature associated with the reference thermal response value.

The electrical machine may be a motor or a generator.

The changing of the speed may be a step change.

The changing of the speed may preferably be an increase in speed.

According to one embodiment it is concluded in step f) that the performance of the lubricant has degraded in case the thermal response value is smaller than the reference thermal response value. A temperature change in the outer bearing ring is not only attributed to the condition of the lubricant but also to that of the electrical machine, the temperature sensor, ambient temperature as well as the fan speed. In all these cases, the temperature coefficient is positive except for the lubricant, making this case distinguishable. More specifically, when changing the speed while keeping the current as constant as possible, the motor losses have less impact on the temperature variations. On the other hand, when the lubricant has degraded, the thermal response is affected more by the fan speed change than by the heat transferred from the bearing balls. Thus, by determining a smaller thermal response value than the reference thermal response value, lubricant performance degradation may be isolated from other reasons causing temperature variations. The performance of the lubricant can thereby be detected in the above-mentioned first phase, and issues with the bearings may thus be detected at an early stage before mechanical failure.

According to one embodiment step e) involves determining the algebraic sum of or difference between the reference thermal response value and the thermal response value.

It has been found that an algebraic sum of or difference gives a more accurate measure of the performance of the lubricant under certain circumstances, because under some operating conditions the reference thermal response value or the thermal response value may be 0, and the ratio between the reference thermal response value and the thermal response value will in such situations not give any useful information about the lubricant.

In case the algebraic sum is smaller than a threshold value or the algebraic difference is larger than a threshold value, it may in step f) be concluded that the performance of the lubricant has degraded. Minor variations in the thermal response value which may occur due to other reasons than degradation of the performance of the lubricant may thus be discarded, resulting in more accurate detection.

The algebraic sum is herein defined as an operation of the type A+B, where A and B are real numbers. The algebraic difference, or simply "difference", is herein defined as an operation of the type A-B, where A and B are real numbers.

In one example step e) involves determining the ratio between the reference thermal response value and the thermal response value.

According to one example a trend of the magnitude of the algebraic sum, difference, or ratio may be determined by comparison with the magnitude of the algebraic sum, difference, or ratio from a previous execution of the method. The conclusion in step f) may in this case be based on whether the magnitude increases or decreases.

According to one embodiment the thermal response value is a linear temperature slope determined further based on the time for reaching the second outer bearing ring temperature from the first outer bearing ring temperature.

The outer bearing ring temperature may have a non-linear oscillating step response before settling after speed of the electrical machine has changed. The first outer bearing ring temperature may for example be selected to be the temperature at a first predefined level, such as 10%, from an initial steady state outer bearing ring temperature or from a minimum temperature, before the speed change. The second outer bearing ring temperature may be selected to be at second predefined level, such as 90%, of a final steady state outer bearing ring temperature of the outer bearing ring achieved after the speed change.

The outer bearing ring temperature may be sampled at a plurality of occasions before, during and after the speed change, to be able to select an appropriate value for the first outer bearing ring temperature and the second outer bearing ring temperature.

According to one embodiment the thermal response value is a thermal time constant determined using a first-order thermal model. In this case, the method may further involve determining whether the second outer bearing ring temperature is lower than the first outer bearing ring temperature and/or whether the linear temperature slope in the current execution of the method has a different sign compared to the occasion when the reference thermal response was determined. Thermal time constants may not be comparable in case the linear temperature slopes associated with the thermal time constants have different signs. In such a case, the linear temperature slope determined based on the first outer bearing ring temperature and the second outer bearing ring temperature, or the difference between the first outer bearing ring temperature and the second outer bearing ring temperature should be used before comparing the thermal time constants. In case it is determined that the sign of the linear temperature slopes differs, any one of the other available thermal response values e.g., the linear temperature slope or temperature difference should be used to draw a conclusion in step f).

The first order thermal model is a thermal model including the outer bearing ring.

According to one embodiment the thermal response value is the difference between the first outer bearing ring temperature and the second outer bearing ring temperature.

One embodiment comprises g) generating an alert in case it has been concluded that the performance of the lubricant has degraded.

According to one embodiment the reference thermal response value was determined under the same operating conditions as the thermal response value. There may thus be a plurality of reference thermal response values stored, with the comparison of the thermal reference being made with a reference thermal reference that has been determined under the same operating conditions as the current execution of the method.

The thermal response value and the reference thermal response value are of the same type. Thus, if for example the thermal response value is the difference between the first outer bearing ring temperature and the second outer bearing ring temperature, the reference thermal response value has been determined by the difference between a reference first outer bearing ring temperature and a reference second outer bearing ring temperature, before and after a speed change of the same magnitude, sign, and starting from the same initial speed.

According to one embodiment in step b) the changing of the speed is from an initial speed of at most 50%, such as at most 40%, such as at most 30%, such as at most 25% of the nominal speed of the electrical machine. By performing the speed change at lower speeds relative to the nominal speed of the electrical machine, the temperature variation can better be isolated from other phenomena such as the impact by the fan.

According to one embodiment the reference thermal response value is indicative of a non-degraded lubricant. The reference thermal response value has in this case thus been determined when the electrical machine or at least the lubricant is healthy.

According to one embodiment step c) is performed when a steady-state outer bearing ring temperature has been reached. A steady-state outer bearing ring temperature has been reached when samples of the outer bearing temperature stay within a window with a predefined upper and lower threshold for a predetermined amount of time.

According to one embodiment prior to step a) the method comprises: i) obtaining a first reference bearing outer temperature, ii) changing the speed of the electrical machine with the same amount, rotational direction, and from the same operational speed as in step b), iii) obtaining a reference second outer bearing ring temperature when the speed has changed, and iv) determining the reference thermal response value based on the reference first outer bearing ring temperature and the reference second outer bearing ring temperature.

Steps i)-iv) may for example be performed during commissioning of the electrical machine, or at a later stage when the electrical machine has been set in operation. In the latter case, steps i)-iv) may be carried out either online, or offline during machine testing.

There is according to a second aspect provided a computer program comprising computer code which when executed by processing circuitry of a control system causes the control system to perform the steps of the method of the first aspect.

There is according to a third aspect provided a control system for detecting degradation of a lubricant in a bearing of an electrical machine, comprising: processing circuitry, and a storage medium comprising a computer code, which when executed by the processing circuitry causes the control system to: a) obtain a first outer bearing ring temperature, b) change the speed of the electrical machine, c) obtain a second outer bearing ring temperature when the speed has changed), d) determine a thermal response value based on the first outer bearing ring temperature and the second outer bearing ring temperature, e) compare the thermal response value with a reference thermal response value for the same speed change as in step b), and f) in case the thermal response value differs from the reference thermal response value, conclude that the performance of the lubricant has degraded.

According to one embodiment in step f) the processing circuitry is configured to conclude that the performance of the lubricant has degraded in case the thermal response value is smaller than the reference thermal response value.

According to one embodiment in step e) the processing circuitry is configured to determine the algebraic sum of or difference between the reference thermal response value and the thermal response value.

According to one embodiment the thermal response value is a linear temperature slope determined further based on the time for reaching the second outer bearing ring temperature from the first outer bearing ring temperature.

According to one embodiment the thermal response value is a thermal time constant determined using a first-order thermal model.

According to one embodiment the thermal response value is the difference between the first outer bearing ring temperature and the second outer bearing ring temperature.

According to one embodiment the processing circuitry is configured to g) generate an alert in case it has been concluded that the performance of the lubricant has degraded.

According to one embodiment the reference thermal response value was determined under the same operating conditions as the thermal response value.

According to one embodiment the processing circuitry is configured to change the speed in step b) from an initial speed of at most 50%, such as at most 40%, such as at most 30%, such as at most 25% of the nominal speed of the electrical machine.

According to one embodiment the reference thermal response value is indicative of a non-degraded lubricant.

According to one embodiment the processing circuitry is configured to perform step c) when a steady-state outer bearing ring temperature has been reached.

According to one embodiment prior to step a) the processing circuitry is configured to: i) obtain a first reference bearing outer temperature, ii) change the speed of the electrical machine with the same amount, rotational direction, and from the same operational speed as in step b), iii) obtain a reference second outer bearing ring temperature when the speed has changed, and iv) determine the reference thermal response value based on the reference first outer bearing ring temperature and the reference second outer bearing ring temperature.

There is according to a fourth aspect provided an electrical machine assembly comprising: an electrical machine provided with a bearing including an outer bearing ring, a temperature sensor configured to measure the temperature of the outer bearing ring, and a control system according to the third aspect configured to receive measurements of an outer bearing ring temperature from the temperature sensor and configured to control the electrical machine.

The electrical machine assembly may comprise a power converter such as a drive, wherein the control system is configured to control the electrical machine via the power converter.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
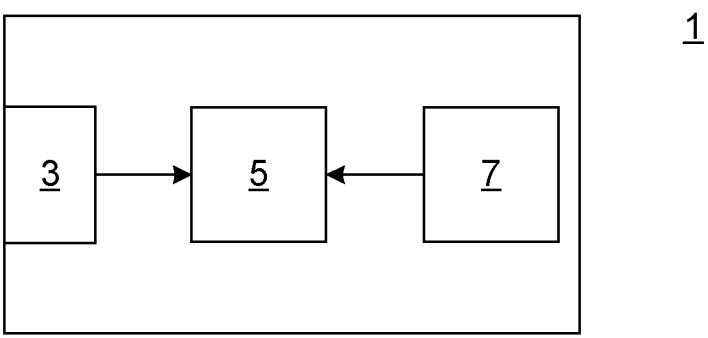
FIG. 1 diagrammatically shows an example of a control system for detecting degradation of a lubricant in a bearing of an electrical machine.

FIG. 1 depicts a block diagram of an example of a control system 1. The control system 1 is configured to control a power converter that controls an electrical machine.

The control system 1 comprises an input unit 3 configured to receive measurements of an outer bearing ring temperature from a temperature sensor.

The control system 1 comprises processing circuitry 5. The control system 1 may further comprise a storage medium 7 comprising a computer code. The processing circuitry 5 may be configured to execute the computer code, to detect degradation of a lubricant of a bearing based on the outer bearing ring temperature received by the input unit 3.

The processing circuitry 5 may for example use any combination of one or more of a suitable central processing unit (CPU), multiprocessor, microcontroller, digital signal processor (DSP), application specific integrated circuit (ASIC), field programmable gate arrays (FPGA) etc., capable of executing any herein disclosed operations concerning lubricant performance monitoring or detection.

The storage medium 7 may for example be embodied as a memory, such as a random access memory (RAM), a read-only memory (ROM), an erasable programmable read-only memory (EPROM), or an electrically erasable programmable read-only memory (EEPROM) and more particularly as a non-volatile storage medium of a device in an external memory such as a USB (Universal Serial Bus) memory or a Flash memory, such as a compact Flash memory.

Figure 2:
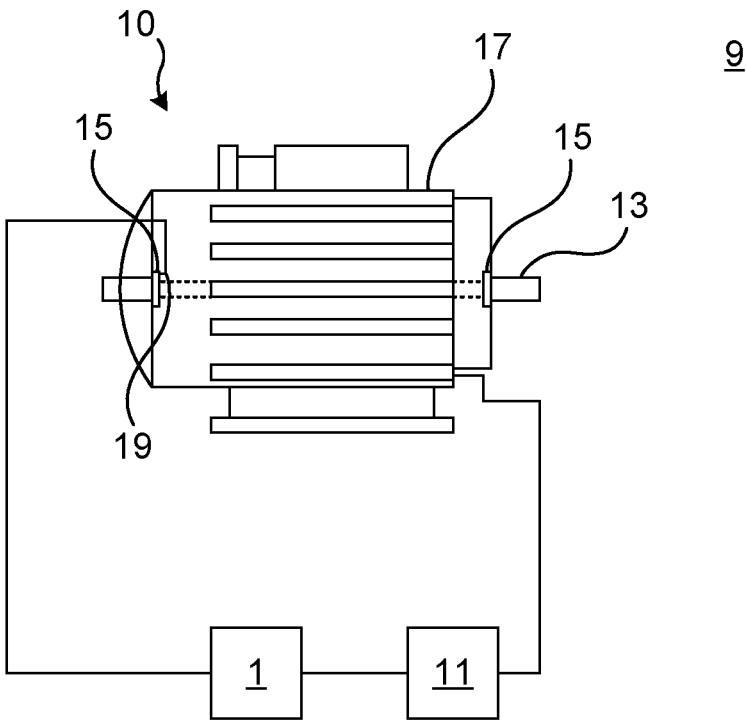
FIG. 2 schematically shows a machine assembly including an electrical machine and the control system in FIG. 1.

FIG. 2 shows an electrical machine assembly 9. The electrical machine assembly 9 comprises an electrical machine 10, the control system 1 and a power converter 11. The control system 1 is configured to control the power converter 11 to thereby control the speed of the electrical machine 10.

The electrical machine 10 comprises a stator and a rotor (not shown) configured to electromagnetically interact with the stator. The rotor comprises a rotor shaft 13. The electrical machine 10 comprises bearings 15 arranged at the ends of the rotor shaft 13 to enable rotation of the rotor.

Each bearing 15 may have an inner bearing ring, an outer bearing ring and a plurality of rolling elements such as balls arranged to roll between the inner bearing ring and outer bearing ring.

The bearings 15 furthermore comprise a lubricant. The lubricant may for example be grease, oil or polymer based.

The electrical machine 10 has a housing 17. The stator and the rotor are arranged in the housing 17. The housing 17 may be configured to bear the weight of the rotor. The inner bearing ring is attached to the rotor shaft 13 and the outer bearing ring may be attached to and/or supported by the housing 17.

The electrical machine assembly 9 comprises a temperature sensor 19 configured to measure the outer bearing ring temperature, i.e. the temperature of the outer bearing ring of one of the bearings 15. The temperature sensor 19 may be directly connected to the outer bearing ring or to the housing 17 in a region close to the outer bearing ring, for measuring the outer bearing ring temperature.

The temperature sensor 19 may be configured to measure the outer bearing ring temperature at a non-driving side of the electrical machine 10 or at the driving side of the electrical machine 10. According to one example, there may be provided temperature sensors 19 configured to measure the outer bearing ring temperature of both bearings 15. In the latter case, the method may be carried out individually for the temperature measurements from both temperature sensors.

The control system 1 is configured to receive measurements of the outer bearing ring temperature from the temperature sensor 19. The control system 1 is configured to detect degradation of a lubricant based on the outer bearing ring temperature measured by the temperature sensor 19, as will be explained in more detail in the following.

Figure 3:
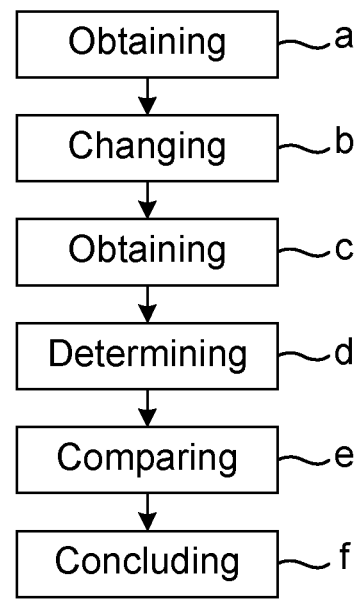
FIG. 3 is a flowchart of a method of detecting degradation of a lubricant in a bearing of an electrical machine.

A method carried out by the control system 1 will now be described with reference to FIG. 3.

In a step a) a first outer bearing ring temperature is obtained by the processing circuitry 5 from measurements of the first outer bearing ring temperature by the temperature sensor 21.

During step a) the electrical machine 10 may be operated at a speed that is e.g., at most 50%, such as at most 40%, such as at most 30%, such as at most 25% of the nominal speed of the electrical machine 10.

In a step b) the speed of the electrical machine 10 is changed. The control system 1 thus sends a new speed reference to the power converter 11 to change the speed of the electrical machine 10.

The speed change may be a step change of the speed at which the electrical machine 10 is operated during step a).

The speed change may for example be an increase of one quarter of the nominal speed of the electrical machine 10. Thus, for example, if the speed of the electrical machine is at 25% of the nominal speed in step a), then the speed change in step b) may result in a speed of 50% of the nominal speed.

In a step c) a second outer bearing ring temperature is obtained by the processing circuitry 5 from measurements of the second outer bearing ring temperature by the temperature sensor 21 after the speed of the electrical machine 10 has changed.

The temperature sensor 19 may capture the outer bearing ring temperature at multiple occasions before the speed change and after the speed change. For example, the temperature sensor 19 may be configured to capture the outer bearing ring temperature at a frequency in the range of 1-100 Hz.

Step a) of obtaining may involve selecting the first outer bearing ring temperature to be a sample at a first predefined level from an initial steady state outer bearing ring temperature before the speed change. Step c) of obtaining may involve selecting the second outer bearing ring temperature to be at second predefined level relative to a final steady state outer bearing ring temperature of the outer bearing ring achieved after the speed change.

In a step d) a thermal response value of the outer bearing ring is determined based on the first outer bearing ring temperature and the second outer bearing ring temperature.

The thermal response value is a value of a thermal response of the outer bearing ring due to the speed change.

The thermal response value may according to one example be a linear temperature slope determined based on the second outer bearing ring temperature, the first outer bearing ring temperature and the time between the two measurements. In mathematical terms the linear temperature slope k is expressed as $k = (T - T_0)/(t - t_0)$, where T is the second outer bearing ring temperature, $T_0$ is the first outer bearing ring temperature, t is the time at which the measurement of the second outer bearing ring temperature occurred and to is the time at which the measurement of the first outer bearing ring temperature occurred.

According to one example, the thermal response value may be the difference between the first outer bearing ring temperature and the second outer bearing ring temperature, i.e. $T - T_0$.

According to one example, the thermal response value is a thermal time constant $\tau$ determined using a first-order thermal model, with the first outer bearing ring temperature and the second bearing ring temperature being inputs to the first-order thermal model. For example, the processing circuitry 5 may be configured to determine the thermal time constant $\tau$ based on the equation $T = (T_0 - T)\exp(t/\tau) + T_{ambient}$, where $T_{ambient}$ is the ambient temperature.

In a step e) the thermal response value is compared with a reference thermal response value. The reference thermal response value has previously been determined for the same speed change as in step b), and preferably from the same initial speed which the electrical machine was operating at before the speed change in step b). With same speed change is to be understood both magnitude and sign, i.e. increase or decrease, of the speed change.

The comparison in step e) may for example involve taking the algebraic sum of or difference between the thermal response value and the reference thermal response value and determining whether the result has passed a threshold.

In a step f) in case the thermal response value differs from the reference thermal response value, the processing circuitry 5 concludes that the performance of the lubricant has degraded. For example, the conclusion may be provided in case the algebraic sum is smaller than a threshold value or in case the algebraic difference is larger than a threshold value.

As an example, it is assumed that the thermal response value is the difference between the first outer bearing ring temperature and the second outer bearing ring temperature, and that the lubricant performance has degraded. In this example, the first outer bearing ring temperature is 30° C. and the second outer bearing ring temperature is 28° C. The thermal response value $T-T_0$ is in this case 28-30° C.=-2° C. If we assume that in the reference case, the outer bearing ring temperature instead increased from 30° C. to 32° C. then the reference thermal response value is $T_{ref}-T_{0ref}$=32-30° C.=2. The algebraic difference between the reference thermal response value and the thermal response value is 2-(-2)=4. In case no degradation of the lubricant would have occurred, it would be expected that the algebraic difference would be 0 because the thermal response value would be the same as the reference thermal response value in case the operating conditions of the electrical machine are identical or essentially identical. The more the temperature decreases in the case of degraded lubricant performance, the larger the algebraic difference will be. This would also be the case if the outer bearing ring temperature does not decrease but increases less than in the reference case. The same applies also for the case of the linear temperature slope.

The above example with an algebraic sum of the thermal response value and the reference thermal response value is 2+(-2)=0. In this case, the expected result would be twice the reference thermal response value, i.e. 4, in case the lubricant would not have degraded.

When the method is executed, the first bearing outer ring temperature, the second bearing outer ring temperature, the initial speed, the speed change, and the ambient temperature may be stored in the storage medium 7 and associated with each other. The thermal reference value may also be stored with the aforementioned parameter values. Further, the root mean square (RMS) phase current may also be stored in the storage medium 7.

The control system 1 may be configured to generate an alert in a step g) in case it has been concluded in step f) that the performance of the lubricant has degraded.

Before steps a)-f) or a)-g), the method may involve performing steps i)-iv) to determine a reference thermal response value. This may for example be during commissioning of the electrical machine 10, or it may be an earlier iteration corresponding to steps a)-e) when the electrical machine 10 is online or offline after commissioning. Thus, in a step i) a first reference bearing outer temperature is obtained, in a step ii) the speed of the electrical machine is changed, in a step iii) a reference second outer bearing ring temperature is obtained when the speed has changed, and in a step iv) the reference thermal response value is determined based on the reference first outer bearing ring temperature and the reference second outer bearing ring temperature. The operation conditions such as initial speed, amount and sign of speed change, ambient temperature etc., are stored together with the reference thermal response value for use under the same conditions in a future comparison in step e) of the method.

Figure 4A:
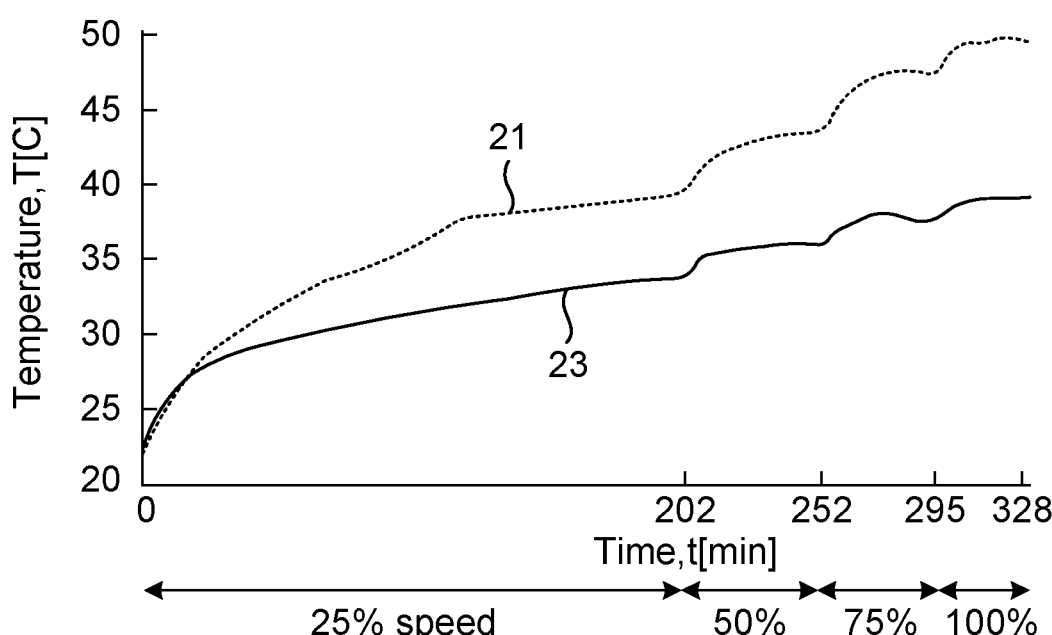
FIG. 4*a* is a graph of temperature measurements during speed changes of an electrical machine with non-degraded lubrication.

With reference to FIG. 4*a* a graph is shown with measurements of the outer bearing ring temperature when the lubricant has no degradation, with a 25% load on the electrical machine. A first curve 21 shows the outer bearing ring temperature at the power converter end of the electrical machine and a second curve 23 shows the outer bearing ring temperature at the non-power converter end of the electrical machine. In both cases, the electrical machine is first operated at 25% of the nominal speed, wherein a speed change is made so that the electrical machine reaches 50% of the nominal speed, 75% of the nominal speed, and then 100% of the nominal speed. As can be seen, both temperature sensors measure a temperature increase as the speed increases.

Figure 4B:
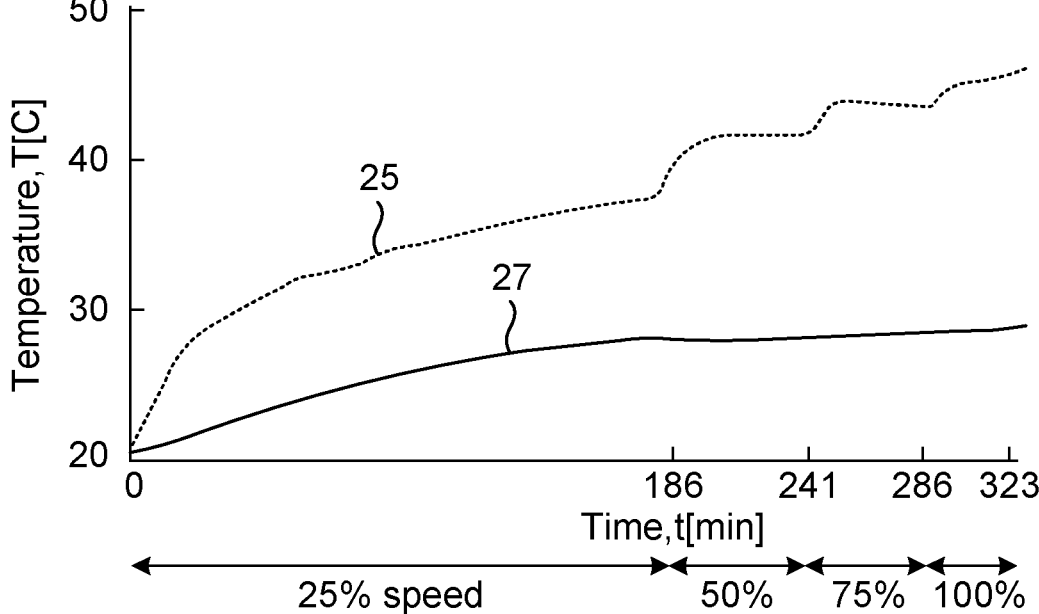
FIG. 4*b* is a graph of temperature measurements during speed changes of an electrical machine with a lubricant with degraded performance.

In FIG. 4*b* a graph is shown with measurements of the outer bearing ring temperature when the lubricant has degraded, and the electrical machine has a 25% load. A third curve 25 shows the outer bearing ring temperature at the power converter end of the electrical machine and a fourth curve 27 shows the outer bearing ring temperature at the non-power converter end of the electrical machine. In both cases, the electrical machine is first operated at 25% of the nominal speed, wherein a speed change is made so that the electrical machine reaches 50% of the nominal speed, 75% of the nominal speed, and then 100% of the nominal speed. As can be seen, the temperature sensor which is arranged at the non-power converter end of the electrical machine measures a temperature decrease in the outer bearing ring temperature as the speed increases, especially at the speed change from 25% of the nominal speed to 50% of the nominal speed. The temperature sensor at the power converter end also measures a decrease in the outer bearing ring temperature of the power converter end bearing, but here the decrease is relative to the outer bearing ring temperature after the speed change in the healthy case shown in FIG. 4*a*.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A method of detecting degradation of a lubricant in a bearing of an electrical machine, comprising:
   a) obtaining, via a temperature sensor, a first outer bearing ring temperature,
   b) operating a power converter to change the speed of the electrical machine,
   c) obtaining, via the temperature sensor, a second outer bearing ring temperature when the speed has changed,
   d) determining a thermal response value of the outer bearing ring based on the first outer bearing ring temperature and the second outer bearing ring temperature,
   e) comparing the thermal response value with a reference thermal response value for the same speed change as in step b), and
   f) in case the thermal response value differs from the reference thermal response value, generating a control signal to trigger an alert indicative of lubricant degradation.

2. The method as claimed in claim 1, wherein step f) comprises concluding that the performance of the lubricant has degraded in case the thermal response value is smaller than the reference thermal response value.

3. The method as claimed in claim 2, wherein step e) involves determining the algebraic sum of or difference between the reference thermal response value and the thermal response value.

4. The method as claimed in claim 2, wherein the thermal response value is a linear temperature slope determined further based on the time for reaching the second outer bearing ring temperature from the first outer bearing ring temperature.

5. The method as claimed in claim 2, wherein the thermal response value is a thermal time constant determined using a first-order thermal model.

6. The method as claimed in claim 2, wherein the thermal response value is the difference between the first outer bearing ring temperature and the second outer bearing ring temperature.

7. The method as claimed in claim 1, wherein step e) involves determining the algebraic sum of or difference between the reference thermal response value and the thermal response value.

8. The method as claimed in claim 1, wherein the thermal response value is a linear temperature slope determined further based on the time for reaching the second outer bearing ring temperature from the first outer bearing ring temperature.

9. The method as claimed in claim 1, wherein the thermal response value is a thermal time constant determined using a first-order thermal model.

10. The method as claimed in claim 1, wherein the thermal response value is the difference between the first outer bearing ring temperature and the second outer bearing ring temperature.

11. The method as claimed in claim 1, wherein the reference thermal response value was determined under the same operating conditions as the thermal response value.

12. The method as claimed in claim 1, wherein in step b) the changing of the speed is from an initial speed of at most 50%, such as at most 40% of the nominal speed of the electrical machine.

13. The method as claimed in claim 1, wherein the reference thermal response value is indicative of a non-degraded lubricant.

14. The method as claimed in claim 1, wherein step c) is performed when a steady-state outer bearing ring temperature has been reached.

15. The method as claimed in claim 1, wherein prior to step a) the method comprises: i) obtaining a first reference bearing outer temperature, ii) changing the speed of the electrical machine with the same amount, rotational direction, and from the same operational speed as in step b), iii) obtaining a reference second outer bearing ring temperature when the speed has changed, and iv) determining the reference thermal response value based on the reference first outer bearing ring temperature and the reference second outer bearing ring temperature.

16. The method as claimed in claim 1, wherein step f) comprises generating a control signal to adjust an operating parameter of the electrical machine to mitigate lubrication degradation in case the thermal response value differs from the reference thermal response value.

17. A computer program product comprising:
a non-transitory computer readable medium; and
a computer program stored in the computer readable medium, the computer program including computer code which when executed by processing circuitry of a control system causes the control system to perform the steps of:
a) obtaining, via temperature sensor, a first outer bearing ring temperature,
b) operating a power converter to change the speed of the electrical machine,
c) obtaining, via the temperature sensor, a second outer bearing ring temperature when the speed has changed,
d) determining a thermal response value of the outer bearing ring based on the first outer bearing ring temperature and the second outer bearing ring temperature, e) comparing the thermal response value with a reference thermal response value for the same speed change as in step b), and
f) in case the thermal response value differs from the reference thermal response value, generating a control signal to trigger an alert indicative of lubricant degradation.

18. A control system for detecting degradation of a lubricant in a bearing of an electrical machine, comprising:
processing circuitry, and
a storage medium having a computer code, which when executed by the processing circuitry causes the control system to perform the steps of:
a) obtaining, via a temperature sensor, a first outer bearing ring temperature,
b) operating a power converter to change the speed of the electrical machine,
c) obtaining, via the temperature sensor, a second outer bearing ring temperature when the speed has changed,
d) determining a thermal response value of the outer bearing ring based on the first outer bearing ring temperature and the second outer bearing ring temperature,
e) comparing the thermal response value with a reference thermal response value for the same speed change as in step b), and
f) in case the thermal response value differs from the reference thermal response value, generating a control signal to trigger an alert indicative of lubricant degradation.

19. An electrical machine assembly comprising:
an electrical machine provided with a bearing including an outer bearing ring,
a temperature sensor configured to measure the temperature of the outer bearing ring, and
a control system including:
a processing circuitry,
a storage medium having a computer code, which when executed by the processing circuitry causes the control system to perform the steps of:
a) obtaining, via the temperature sensor, a first outer bearing ring temperature,
b) operating a power converter to change the speed of the electrical machine,
c) obtaining, via the temperature sensor, a second outer bearing ring temperature when the speed has changed,
d) determining a thermal response value of the outer bearing ring based on the first outer bearing ring temperature and the second outer bearing ring temperature,
e) comparing the thermal response value with a reference thermal response value for the same speed change as in step b),
f) in case the thermal response value differs from the reference thermal response value, generating a control signal to trigger an alert indicative of lubricant degradation, and
wherein the control system is configured to receive measurements of an outer bearing ring temperature from the temperature sensor and configured to control the electrical machine.

* * * * *